US012583807B2

(12) United States Patent
Iglesia et al.

(10) Patent No.: US 12,583,807 B2
(45) Date of Patent: Mar. 24, 2026

(54) PRETREATING METAL OXIDE CATALYSTS FOR ALKANE DEHYDROGENATION

(71) Applicant: The Regents of the University of California, Oakland, CA (US)

(72) Inventors: Enrique Iglesia, Berkeley, CA (US); Junnan Shangguan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 67 days.

(21) Appl. No.: 18/319,483

(22) Filed: May 18, 2023

(65) Prior Publication Data

US 2023/0303465 A1 Sep. 28, 2023

Related U.S. Application Data

(63) Continuation of application No. PCT/US2021/063419, filed on Dec. 15, 2021.

(60) Provisional application No. 63/126,525, filed on Dec. 16, 2020.

(51) Int. Cl.
*C07C 5/333* (2006.01)
*B01J 21/06* (2006.01)
*B01J 37/08* (2006.01)

(52) U.S. Cl.
CPC ........... *C07C 5/3332* (2013.01); *B01J 21/066* (2013.01); *B01J 37/08* (2013.01); *C07C 2521/06* (2013.01)

(58) Field of Classification Search
CPC .............................. C07C 5/3332; B01J 21/066
See application file for complete search history.

(56) References Cited

U.S. PATENT DOCUMENTS

| | | | | |
|---|---|---|---|---|
| 4,410,751 A | * | 10/1983 | Shin | C07C 1/20 502/242 |
| 4,868,342 A | * | 9/1989 | Verson | C07C 41/06 585/324 |
| 5,308,822 A | * | 5/1994 | Iezzi | B01J 37/14 502/344 |
| 7,045,672 B2 | * | 5/2006 | Xu | C07C 1/20 585/639 |

(Continued)

FOREIGN PATENT DOCUMENTS

| | | | |
|---|---|---|---|
| CN | 104923258 A | * | 9/2015 |
| EP | 1524019 | | 10/2013 |

(Continued)

OTHER PUBLICATIONS

Tatyana Otroshchenko, Dr. Sergey Sokolov, Dr. Mariana Stoyanova, Dr. Vita A. Kondratenko, Dr. Uwe Rodemerck, Dr. David Linke , Priv.-Doz. Dr. Evgenii V. Kondratenko, ZrO2-Based Alternatives to Conventional Propane Dehydrogenation Catalysts, 2015, Angew. Chem. Int. Ed. 54, 15880-15883 (Year: 2015).*

(Continued)

*Primary Examiner* — Ellen M McAvoy
*Assistant Examiner* — Ming Cheung Po
(74) *Attorney, Agent, or Firm* — Richard Aron Osman

(57) ABSTRACT

Catalytic dehydrogenation of a light alkane gas on a metal oxide catalyst is achieved by (a) pretreating the metal oxide catalyst with dimethylether (DME); and (b) reacting the alkane gas catalytically on the catalyst in a dehydrogenation reaction, under conditions wherein the pretreating improves product yield of the reaction.

17 Claims, 7 Drawing Sheets

(56)                   References Cited

U.S. PATENT DOCUMENTS

| | | | | |
|---|---|---|---|---|
| 7,199,277 | B2 * | 4/2007 | Xu ........................... | C07C 1/20 |
| | | | | 502/263 |
| 11,253,845 | B2 * | 2/2022 | Ide .......................... | B01J 35/56 |
| 2005/0101815 | A1 * | 5/2005 | Xu ........................... | C07C 1/20 |
| | | | | 585/639 |
| 2006/0133977 | A1 * | 6/2006 | Male ....................... | B01J 37/16 |
| | | | | 423/239.1 |

FOREIGN PATENT DOCUMENTS

| | | | | |
|---|---|---|---|---|
| WO | 2019051101 | 3/2019 | | |
| WO | WO-2019051101 A1 * | 3/2019 | ............. | B01J 21/02 |

OTHER PUBLICATIONS

Machine Translation of Description of CN104923258A (Year: 2015).*
International Search Report for priority PCT/US21/63419, 9 pages (Mar. 1, 2022).
Extended European Search Report for related EP 21907678.3, 6 pages (May 15, 2024).
Tatyana Otroshchenko et al: "ZrO2-Based Alternatives to Conventional Propane Dehydrogenation Catalysts: Active Sites, Design, and Performance", Angewandte Chemie International Edition, Verlag Chemie, Hoboken, USA, vol. 54, No. 52, Nov. 13, 2015 (Nov. 13, 2015), pp. 15880-15883.

\* cited by examiner

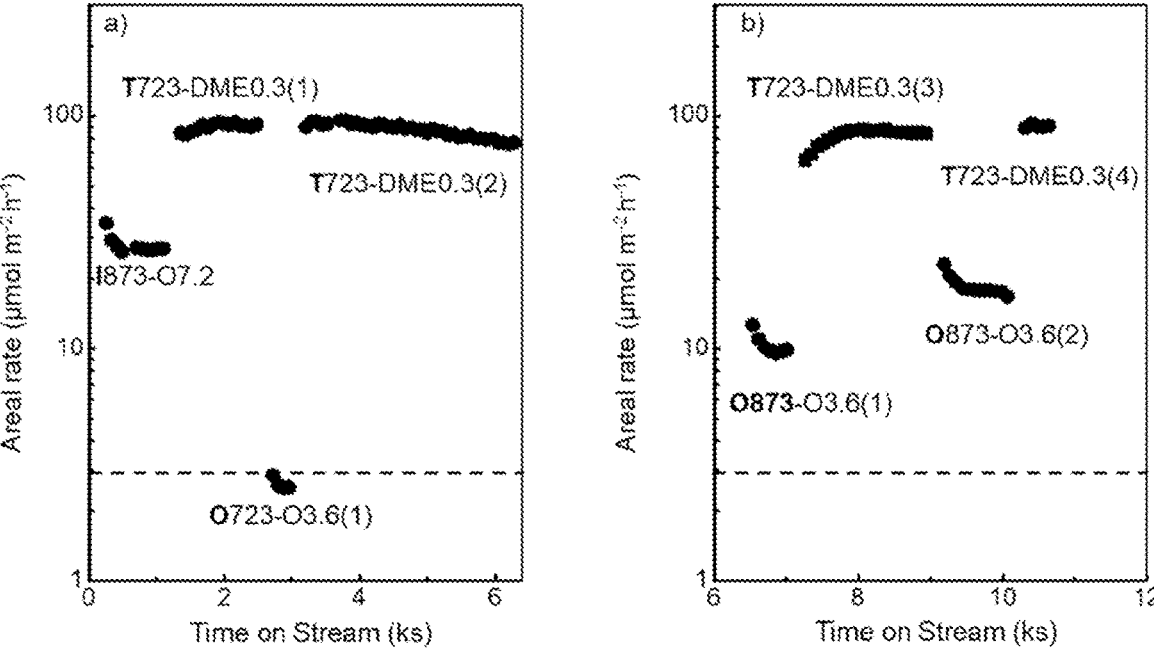
Fig. 8a                                   Fig. 8b
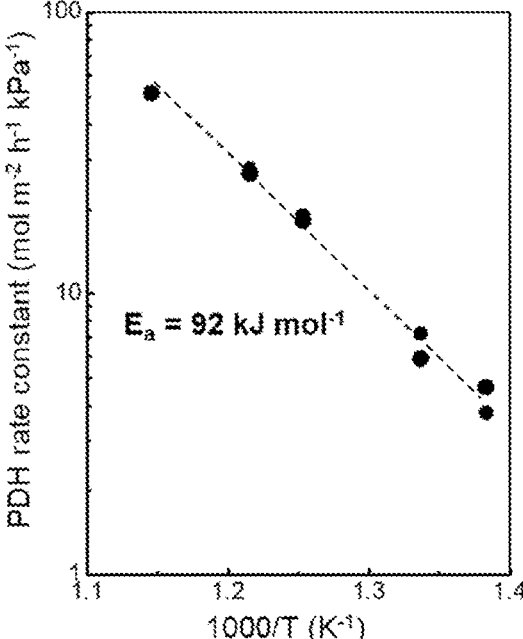
Fig. 9

PRETREATING METAL OXIDE CATALYSTS FOR ALKANE DEHYDROGENATION

INTRODUCTION

Dehydrogenation of light alkanes has been shown to occur on earth-abundant metal oxides. $ZrO_2$ catalysts have been shown to catalyze propane dehydrogenation (PDH) and exhibit an initial dehydrogenation activity at 823 K of about 5 mol $kg^{-1}h^{-1}$, which increases to about 11 mol $kg^{-1}h^{-1}$ after 7 h on stream (40 kPa $C_3H_8$ in $N_2$) in the absence of co-fed $H_2$ [1]. CO pretreatment (57 kPa) of $ZrO_2$ at 823 K for 0.5 h leads to a seven-fold rate enhancement of PDH rates (823 K, 40 kPa $C_3H_8$ in $N_2$). CO temperature programmed reduction (CO-TPR, 1 kPa CO) from ambient temperature to 1173 K (1.6 K $s^{-1}$) shows significant CO consumption between 723 K to 1173 K [1], a temperature regime where the water-gas shift reaction is known to occur [2]; such treatments may remove the strongly adsorbed surface water that exists in its dissociated state [3, 4]. In spite of such observations, previous studies have attributed these effects of thermal treatments (in $H_2$ or in CO) on reactivity to minority coordinatively unsaturated Zr sites that form during such treatments (in spite of >500 kJ $mol^{-1}$ formation enthalpy of O-vacancies on $ZrO_2$ [1]). Measured activation energy barriers are also much higher (>130 kJ $mol^{-1}$) than those derived from theory on $ZrO_2$ surfaces with O-vacancies (<30 kJ $mol^{-1}$) [1].

SUMMARY OF THE INVENTION

The foregoing observations and inconsistencies in the current literature led us to explore the purposeful treatment of $ZrO_2$ catalysts with propylene (0.5 kPa) or dimethyl ether (DME, 1-10 kPa); these treatments lead to 2-fold and 40-fold increases in PDH rates (723 K, 13.7 kPa propane and 12.3 kPa $H_2$) after propylene (0.5 kPa, 723 K, 1.8 ks) and DME treatments (1-10 kPa, 413-823 K, 0.06-3.6 ks), respectively. After DME pretreatment, the maximum rates measured at 723 K, 13.7 kPa propane, and in the presence of $H_2$ (12.3 kPa) become comparable to those initial rates measured previously at 823 K, 40 kPa propane, and in the absence of $H_2$ [1]. The pretreatment generates Zr—O site pairs and active sites. The propylene formation derived from stoichiometric reaction between any DME-derived carbon deposits and propane is insignificant, as the carbon deposited during DME treatment, measured via post-reaction oxidation, is about 10-fold less than would be required for its use as a stoichiometric propylene formation reaction. The rate enhancements from alkene/DME may originate from the dehydroxylation/decarboxylation of $ZrO_2$ catalysts via alkene/DME reactions with $H_2O/CO_2$ occurring at temperatures much lower than those required for treatments in oxidative [1], reductive [1], or inert environments [1], thus allowing the retention of higher reactive surface areas by preventing sintering that is ubiquitous during treatments at such higher temperatures. The method described here provides a novel approach for preparing high surface area oxides devoid of bound $H_2O$ or $CO_2$, by avoiding the requirement for severe thermal treatments (i.e., treatments without alkenes/ethers) that dehydroxylate/decarboxylate the oxide surface [6].

In one embodiment, this invention provides a method of catalytic dehydrogenation of a light alkane gas (e.g. ethane, propane, n-butane, isobutane, pentane) on a metal oxide (e.g. $ZrO_2$, $TiO_2$, $Al_2O_3$) catalyst, the method comprising: (a) pretreating the metal oxide catalyst with dimethylether (DME); and (b) reacting the alkane gas on the catalyst in a dehydrogenation reaction, under conditions wherein the pretreating improves product yields for this dehydrogenation reaction.

Pretreatment of a catalyst, in the case of the present invention a metal oxide, is to be understood as any process in which a catalyst is contacted with a chemical, combination of chemicals, or a series of chemicals to bring or restore it to a higher activity and/or selectivity state, either before using the catalyst for the intended chemical process or at intervening points in time during use of the catalyst, as shown by the periodic DME treatments that recover the initial activity and involve stopping the PDH reaction and doing again a DME treatment and returning to the PDH feeds. Such pretreatments may be carried out inside or outside the chemical reactor. When used at intervening points during catalyst use, such pretreatments seek to restore all or a portion of the activity and/or selectivity of the catalyst in protocols that may be denoted to those skilled in the art as catalyst regeneration treatments. When used initially upon charging catalysts into a reactor, they may be denoted as activation or selectivation protocols.

In embodiments:
the pretreating is performed at a temperature up to 900 K;
the pretreating is performed at a temperature up to 873 K;
the pretreating is performed at a temperature up to 823 K;
the pretreating is performed at a temperature up to 723 K;
the pretreating is performed at a temperature within a range of 323-900 K;
the pretreating is performed at a temperature within a range of 323-873 K;
the pretreating is performed at a temperature within a range of 323-823 K;
the pretreating is performed at a temperature within a range of 323-723 K;
the alkane is propane;
the metal oxide is $ZrO_2$;
the pretreating improves product yield at least 2-fold compared with a comparable reaction without the pretreating step;
the reaction product is an alkene; and/or
the pretreating step further comprises a pretreatment with oxygen prior to or following the pretreatment with DME.

The invention encompasses all combinations of the particular embodiments recited herein, as if each combination had been laboriously recited.

the magenta dash line indicates the stable activity measured on $ZrO_2$ at 13.7 kPa $C_3H_8$, 12.3 kPa $H_2$, and 723 K before any followed up treatment(s) (FIG. 2); c) Arrhenius plot of the non-oxidative PDH rate per mass of literature reported Cr-based (square symbol, 40 kPa $C_3H_8$), Ru-based (triangle symbol, 40 kPa $C_3H_8$), Pt-based (diamond symbol, 100 kPa $C_3H_8$), and $ZrO_2$ (black circle, 40 kPa $C_3H_8$; the yellow color indicate the $ZrO_2$ pretreatment in 57 kPa of CO) catalysts, and commercial $ZrO_2$ without DME treatment measured in this study (black circle, 13.7 kPa $C_3H_8$), and DME-treated $ZrO_2$ in this study (brown circle, 13.7 kPa $C_3H_8$), where open and closed symbols denote 0 and 12.3 kPa $H_2$ cofed, respectively.

Figures 4A, 4B, 4C:
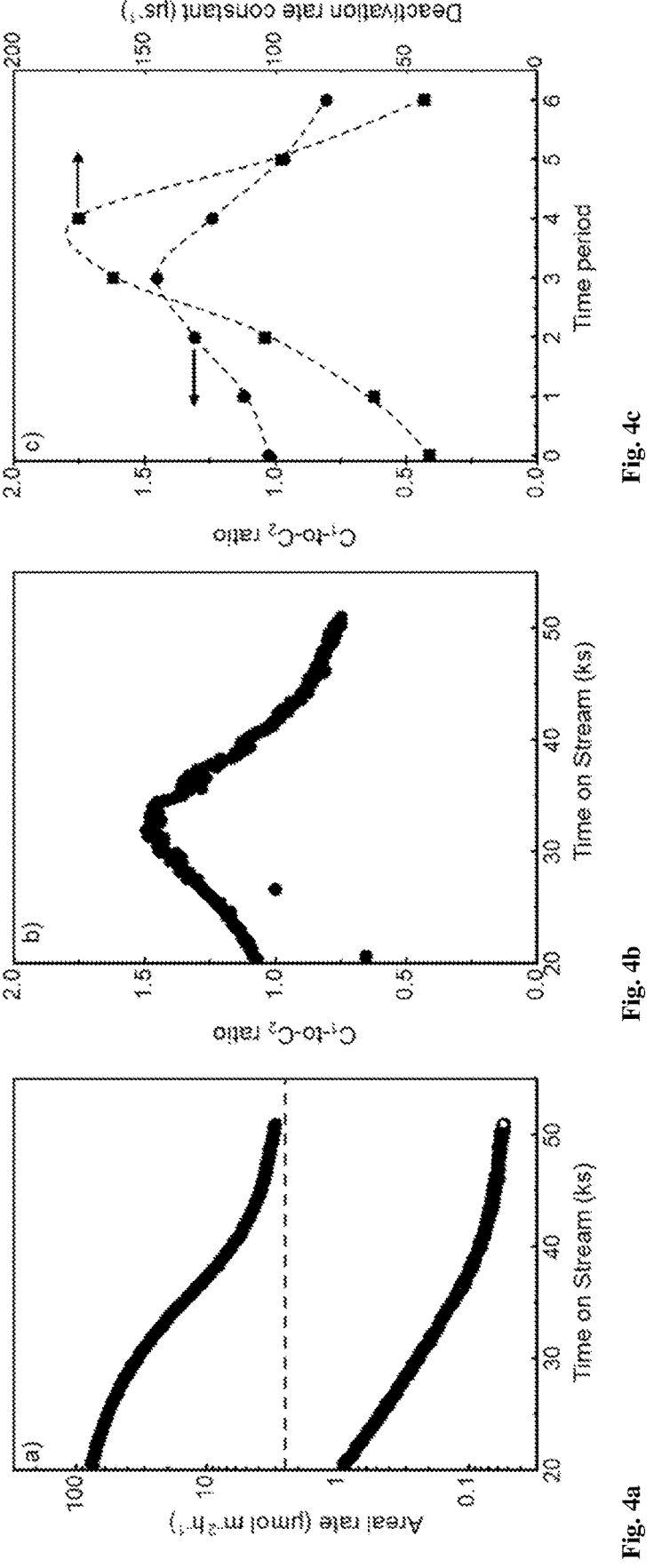

FIGS. 4a-c. a) Propane dehydrogenation rate per initial surface area of catalyst ($r_{f,d}$, solid symbols) and $C_1$ formation rate ($r_{C1}$), and b) $C_1$-to-$C_2$ ratio during propane dehydrogenation reaction on $ZrO_2$ catalyst from 20 ks to 55 ks (13.7 kPa $C_3H_8$, 12.3 kPa $H_2$, 723 K, I723-O7.2); c) time-averaged $C_1$-to-$C_2$ ratio and deactivation rate constant plotted as a function of time period. The Magenta dash line in FIG. 4a indicates the stable activity before measured on $ZrO_2$ at 13.7 kPa $C_3H_8$, 12.3 kPa $H_2$, and 723 K before any followed-up treatment(s).

Figures 5A, 5B, 5C:
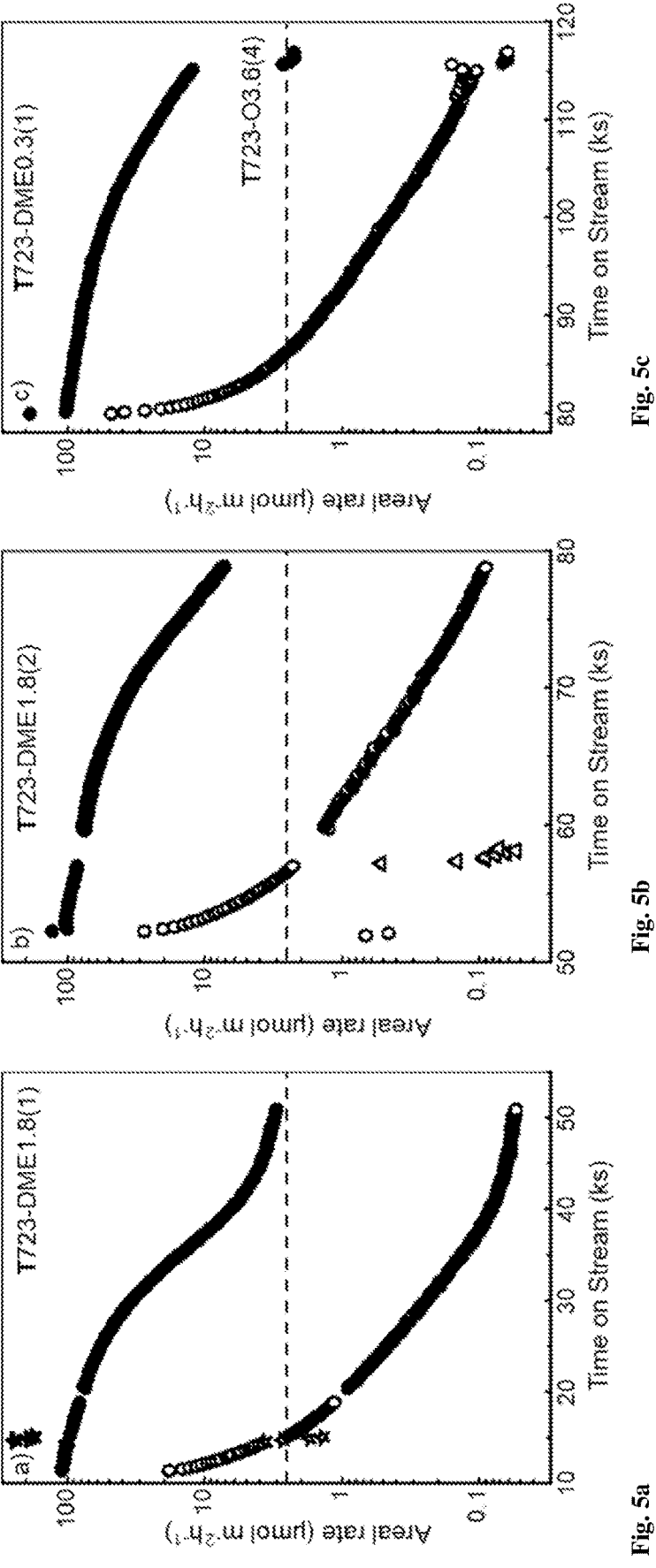

FIGS. 5a-c. Areal PDH ($r_{f,d}$, solid symbols) and $C_1$ formation rate ($r_{C1}$, open symbols) measured after a) first DME treatment (i.e., T723-DME1.8,); b) second DME treatment (i.e., T723-DME1.8(2)); c) third DME treatment (i.e., T723-DME0.3(1), in brown) and after the oxidative treatment (i.e., T723-O3.6(4), in magenta) during propane dehydrogenation reaction on $ZrO_2$ catalyst (I723-O7.2) at 723 K; circle symbol (13.7 kPa $C_3H_8$, 12.3 kPa $H_2$), star symbol (13.7 kPa $C_3H_8$, 0 kPa $H_2$), and triangle symbol (0 kPa $C_3H_8$, 12.3 kPa $H_2$); Magenta dash line in FIGS. 5a-5c indicates the stable activity before measured on $ZrO_2$ at 13.7 kPa $C_3H_8$, 12.3 kPa $H_2$, and 723 K before any followed-up treatment(s).

Figure 6:
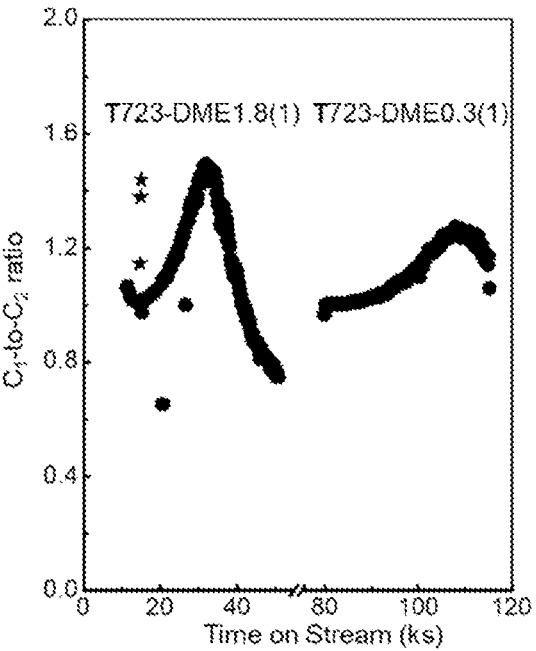

FIG. 6. $C_1$-to-$C_2$ ratio during propane dehydrogenation reaction on $ZrO_2$ catalyst measured after first (i.e., T723-DME1.8(1), in brown) and third (i.e., T723-DME0.3(1), in black) DME treatments.

Figure 7:
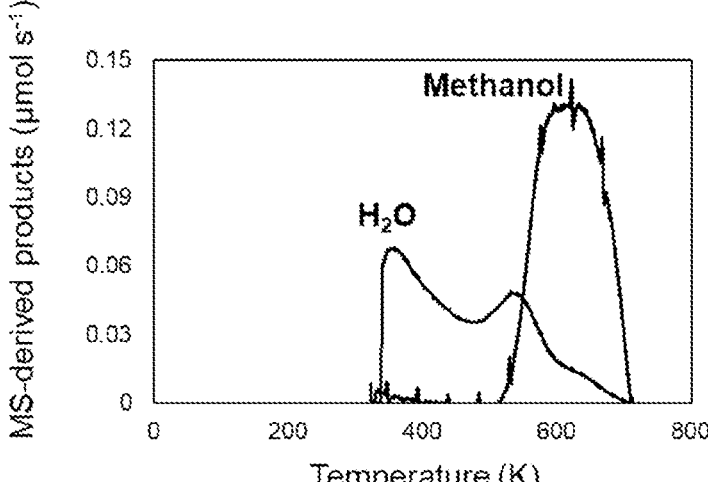

FIG. 7. $H_2O$ (blue) and methanol (yellow) desorption molar rates plotted as a function of temperature during TPD in 1 kPa dimethyl ether (0.83 cm$^3$ s$^{-1}$, 0.5 kPa Ar, balanced with He) of as prepared $ZrO_2$ catalysts (0.2 g, He treated at 323 K) from 323 K to 723 K (0.03 K s$^{-1}$).

Figure 2:
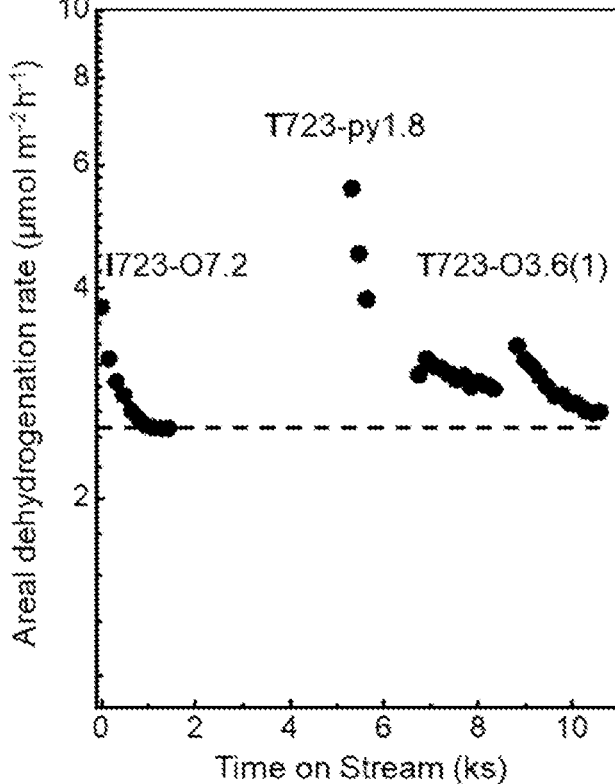
FIG. 2. Areal PDH rate ($r_{f,d}$) during propane dehydrogenation reaction on $ZrO_2$ catalyst (13.7 kPa $C_3H_8$, 12.3 kPa $H_2$, 723 K, I723-O7.2); color indicates the treatment used before the catalytic reaction (Magenta: $O_2$; dark yellow: propylene;) the dashed line indicates the stable activity measured on $ZrO_2$ at 13.7 kPa $C_3H_8$, 12.3 kPa $H_2$, and 723 K before any followed up treatment(s).

FIGS. 8a-b. Areal PDH rates ($r_{f,d}$) of a) after initial $O_2$ pretreatment at 873 K (I873-O7.2, magenta), 10 kPa DME treatment at 723 K (i.e., T823-DME0.3(x), x=1 or 2, brown), and after $O_2$ treatment at 723 K (T723-O3.6(1), magenta) and b) after 10 kPa DME treatment at 723 K (i.e., T823-DME0.3(x), x=3 or 4, brown) and after $O_2$ treatment at 873 K (T873-O3.6(y), y=1 or 2, magenta) measured at 13.7 kPa $C_3H_8$, 12.3 kPa $H_2$, and 723 K on $ZrO_2$ catalyst. Magenta dash line in FIGS. 8 and 8b indicates the stable activity before measured on $ZrO_2$ at 13.7 kPa $C_3H_8$, 12.3 kPa $H_2$, and 723 K, right after pretreated in $O_2$ for 7.2 ks at 723 K (I723-O7.2), as shown in FIG. 2.

FIG. 9. PDH rate constant (13.7 kPa and 12.3 kPa inlet propane and $H_2$ pressure), which is the measured PDH areal rate normalized to the averaged propane pressure, obtained on a DME treated as prepared $ZrO_2$ (1 kPa DME, 0.3 ks) plotted against inverse of temperature.

Figures 10A, 10B, 10C:
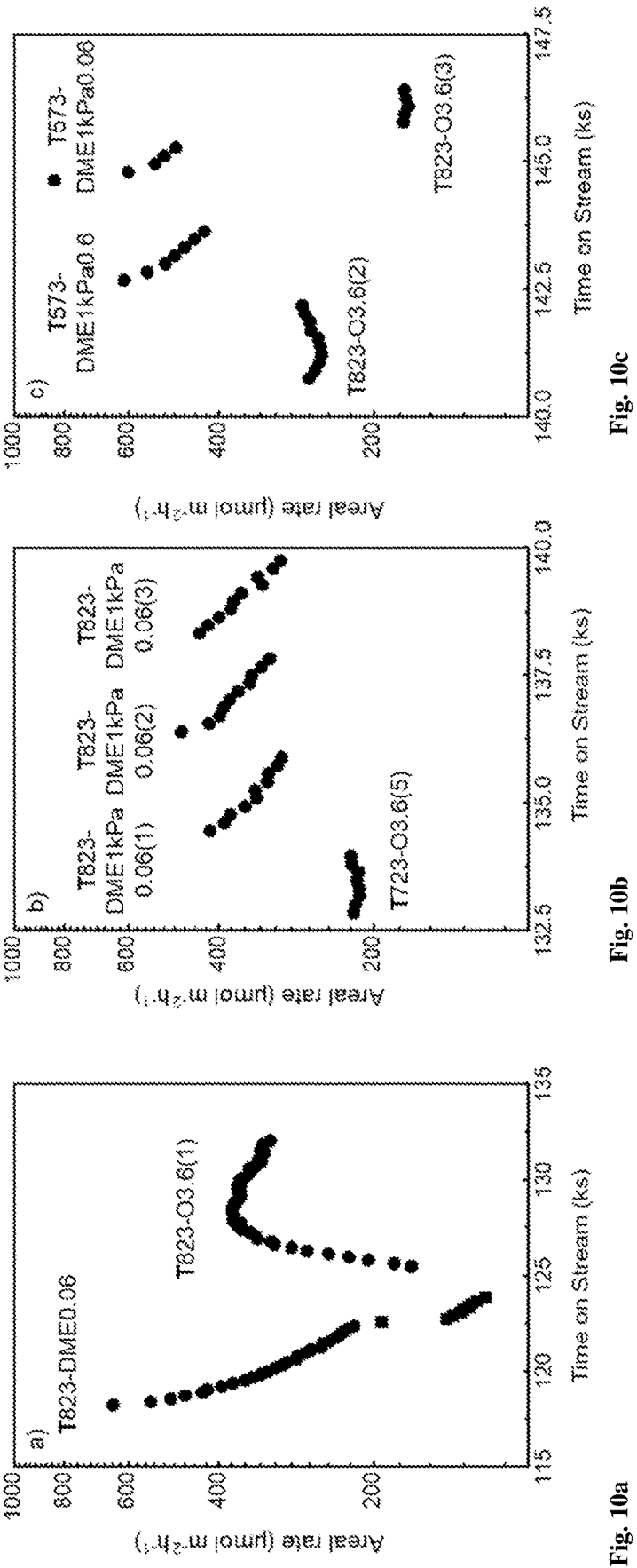

FIGS. 10a-c. Areal PDH rate ($r_{f,d}$) measured after a) DME (10 kPa) treatment at 823 K (i.e., T823-DME0.06, brown) and $O_2$ treatment at 823 K (i.e., T823-O3.6(1), magenta) at 13.7 kPa $C_3H_8$, 12.3 kPa (circle) or 0 kPa (square) $H_2$ and 823 K on $ZrO_2$ catalyst (I723-O7.2), b) $O_2$ treatment at 723

K (i.e., T723-O3.6(5), magenta) and DME treatments at 823 K (1 kPa DME, T823-DME1kPa0.06(x), x=1-3, purple) at 13.7 kPa $C_3H_8$, 12.3 kPa $H_2$, and 823 K, and c) $O_2$ treatment at 823 K (i.e., T823-O3.6(y), y=2 or 3, magenta) and DME treatments at 573 K (1 kPa DME, T573-DME1kPa0.06 or T573-DME1kPa0.6, blue) at 13.7 kPa $C_3H_8$, 12.3 kPa $H_2$, and 823 K.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

In these examples, we demonstrate a strategy to remove the irreversible titrants such as $H_2O$ and $CO_2$ bound on zirconium oxide ($ZrO_2$) as a result of synthetic protocols used to form the catalyst or during subsequent exposure to ambient air; such removal ultimately increases the activity of $ZrO_2$ during propane dehydrogenation (PDH) reactions. $ZrO_2$ catalysts bind $H_2O$ and $CO_2$ titrants from air; these species cannot be completely removed even at temperature above 1173 K, as shown by our temperature programmed experiments. The high temperature thermal treatments required have also been shown to occlude $ZrO_2$ catalyst and reduce the accessible surface area, which leads to lower dehydrogenation reactivity on $ZrO_2$ after such high temperature treatment, despite the removal of these strong surface titrants. Without being bound to any particularly theory, leveraging alkene (e.g. propylene) and ether (e.g., dimethyl ether) reactions with $H_2O/CO_2$ may allow for the removal of surface $H_2O/CO_2$ titrants, thus freeing bare Zr—O sites for alkane dehydrogenation reactions without the destruction of the porous structure and active exposed surface area associated with high temperature treatments, illustrated here using propane dehydrogenation reaction (PDH) as an example, but generally applicable for any reactions catalyzed by stoichiometric Zr—O site pairs. At 723 K, the activity of $ZrO_2$ catalysts increases by approximately 2-fold and 40-fold after propylene (0.5 kPa) and DME (1-10 kPa) treatment at 723 K for 1.8 ks, respectively. The observed promotional effect on PDH rate does not derive from either the decomposition of carbon deposits or the stoichiometric reaction between carbon deposits and propane, as propylene formation is immediately suppressed when turning off the propane feed, and the carbon deposited on $ZrO_2$ via DME treatment is >10 times less than that required for a stoichiometric propylene formation reaction. In particular, DME treatments of $ZrO_2$ catalysts improve the catalyst's activity at 723 K and 13.7 kPa propane to 5 mol kg$^{-1}$h$^{-1}$ (with 12.3 kPa $H_2$) and 10 mol kg$^{-1}$h$^{-1}$ (without $H_2$), which is comparable to values obtained previously at 823 K for $ZrO_2$ catalysts (7 mol kg$^{-1}$h$^{-1}$, at 40 kPa propane without $H_2$ [1]). The PDH reactivity measured at 823 K and 13.7 kPa propane after DME treatment becomes 28 mol kg$^{-1}$h$^{-1}$ (with 12.3 kPa $H_2$), which is more than two-fold higher than on Pt and Cr-based catalysts, even though the latter were measured at higher propane pressure (40 kPa) and in the absence of $H_2$ inhibitor at 823 K. Temperature-programmed reaction studies using DME (1 kPa) confirmed the successful removal of surface hydroxyls by DME hydration reactions, as methanol, the hydration product of DME, continuously evolves at temperatures above 520±5 K. The PDH activation barrier measured on $ZrO_2$ catalysts after DME treatment is 92 kJ $mol^{-1}$, which is much lower than literature reported values (>130 kJ $mol^{-1}$) [1] but is comparable to the value derived from theoretical calculations (106 kJ $mol^{-1}$). These findings confirm that PDH reaction proceeds catalytically on a stoichiometric $ZrO_2$ surface, which is exposed through the assistance of alkene/ether pretreatments. The current strategy leads to reproducible PDH reactivity after DME treatment with or without oxidative treatments. Our methods can be applied to other metal oxide catalysts (e.g., $TiO_2$, $Al_2O_3$) to remove $H_2O/CO_2$ as site titrants, thus exposing their bare surfaces for catalytic reactions without the risks of sintering and loss of active surface area.

Catalyst Synthesis and Catalytic Rate and Selectivity Measurements:

The $ZrO_2$ materials were prepared using a hydrothermal protocol described previously in literature [1] and involves mixing $ZrO(NO_3)_2 \cdot xH_2O$ aqueous solutions (12.3 g in 30 ml deionized water) and urea (21.6 g in 30 ml deionized water) followed by subsequent hydrolysis of urea, and increase in pH and the crystallization of $ZrO_2$ powders (453 K, 20 h), which were dried in ambient air at 383 K overnight. As synthesized catalysts were treated in flowing $O_2$ and He mixture (2 $cm^3$ $g^{-1}s^{-1}$, 4% $O_2$ balanced with He, Praxair) by heating to 723 K (at 0.167 K $s^{-1}$), holding for 2 h hold, and subsequently purging with flowing He (2 $cm^3$ $g^{-1}s^{-1}$, UHP, Praxair) in order to remove residual $O_2$ from the reactor. $C_3H_8$ (50% $C_3H_8$, 10% Ar internal standard, balanced with He, Praxair) and hydrogen (99.999%, Praxair) were introduced into the reactor with He flow (UHP, Praxair) at 723 K. The effluent stream was analyzed by on-line mass spectrometry (MS, MKS) and gas chromatography (GC; Agilent 6890A) using a flame ionization detector (FID) after separation (GS-GASPRO column, Agilent).

Temperature Programmed Oxidation of $ZrO_2$ to 1173 K

The as prepared $ZrO_2$ was treated at 873 K in He and in $H_2$/He before temperature programmed oxidation (TPO) in 4 kPa $O_2$ (balanced with He, 3.35 $cm^3g^{-1}s^{-1}$). The temperature was increased at 0.167 K $s^{-1}$ from 323 K to 873 K in 4 kPa $O_2$ and held for 7.2 ks, before a final ramp from 873 K to 1173 K at 0.167 K $s^{-1}$. After inert and reductive (i.e. 25 kPa $H_2$ in He) treatments, $H_2O$ continued to evolve from the samples, indicative of $H_2O$ molecules that strongly titrate Zr—O Lewis acid-base pairs, consistent with previous reports [4, 7]. In fact, increasing temperature to 1173 K is unable to remove all bound water, as water continues to evolve. Previous reports have shown that high-temperature surface annealing removes surface hydroxyls, but it also leads to pore collapse and loss of surface area. Hence, water, which dissociatively adsorbs on $ZrO_2$ as surface hydroxyls [8], titrates Zr—O site pairs, especially those at the surfaces of monoclinic and tetragonal $ZrO_2$ which are the most reactive.

Effect of Propylene Pretreatment on Propane Dehydrogenation Rate at 723 K

In what follows, we denote the initial pretreatment of $ZrO_2$ catalyst which has not been exposed to other gases except for air at ambient temperature as "I" and the treatment of $ZrO_2$ which has been previously exposed to other gases other than air at ambient temperature as "T". The treatment temperature and duration are denoted as t (t=723-873 K) and δ (δ=0-7.2 ks), respectively. The treatment gaseous condition is denoted as α (α=O, py, DME, as abbreviations for $O_2$, propylene, and dimethyl ether (DME), respectively); the $O_2$, propylene, and DME partial pressure used in these treatments are 4 kPa, 0.5 kPa, and 10 kPa unless otherwise indicated. The number of times that the catalysts have undergone the same treatment is denoted as "(i)" (i=1-5). Thus, It-αδ and Tt-αδ(i) denote initial pretreatment at temperature t in α gas for δ and treatment at identical condition but repeated for the $i^{th}$ time. As an example, T723-O3.6(2) indicates the second, $O_2$ treatment of 3.6 ks at 723 K. Table 1 summarizes the treatment conditions applied in the following discussions.

TABLE 1

Summary of treatment conditions and the associated nomenclature

| Treatment | Duration (ks) | T (K) | Repetition | Nomenclature |
|---|---|---|---|---|
| $O_2$ (pre) | 7.2 | 723 | — | I723-O7.2 |
| | Below for treatments on catalyst I723-O7.2 | | | |
| propylene | 1.8 | 723 | 1st | T723-py1.8 |
| $O_2$ | 3.6 | 723 | i | T723-O3.6(i) |
| $O_2$ | 3.6 | 823 | i | T823-O3.6(i) |
| DME | 1.8 | 723 | i | T723-DME1.8(i) |
| DME | 0.3 | 723 | i | T723-DME0.3(i) |
| DME | 0.06 | 823 | i | T823-DME0.06(i) |
| DME1kPa | 0.06 | 823 | i | T823-DME1kPa0.06(i) |
| DME1kPa | 0.6 | 573 | i | T573-DME1kPa0.6(i) |
| DME1kPa | 0.06 | 573 | i | T573-DME1kPa0.06(i) |
| $O_2$ (pre) | 7.2 | 873 | — | I873-O7.2 |
| | Below for treatments on catalyst I873-O7.2 | | | |
| $O_2$ | 3.6 | 723 | i | T723-O3.6(i) |
| $O_2$ | 3.6 | 873 | i | T873-O3.6(i) |
| DME | 0.3 | 723 | i | T723-DME0.3(i) |

The forward rate of propane dehydrogenation, $r_{f,d}$, is defined as $$r_{f,d} = \frac{r_{net,d}}{1 - \eta_d} \quad (1a)$$

$$\text{where } \eta_d = \frac{Q_d}{K_d} \quad (1b)$$

where $r_{net,d}$, $\eta_d$, $Q_d$, and $K_d$ denote measured net rate, approach to equilibrium, reaction quotient, and equilibrium constant for the PDH reaction at the temperature of interest, respectively. Propane dehydrogenation occurs on $ZrO_2$ catalyst (pretreated in 4% $O_2$/He mixture at 723 K for 2 h, denoted as I723-O7.2) with an initial areal rate of 3.7 µmol $m^{-2}h^{-1}$; this rate decays rapidly and stabilizes at 2.5 µmol $m^{-2}h^{-1}$ after about 1 ks, as shown in FIG. 2. A treatment in propylene (0.5 kPa balanced with He, at 723 K denoted as T723-py1.8), intended to remove surface-bound $H_2O/CO_2$, led to a 2-fold increase in the initial areal PDH rate (i.e., from 3.7 to 5.5 µmol $m^{-2}h^{-1}$). The purposeful removal of propane (13.7 kPa to 0 kPa) from the inlet stream (between 5.6 ks to 6.7 ks time-on-stream) immediately suppressed propylene formation, indicating that the reactivity enhancement conferred by the propylene treatment reflects the reaction between the actual active sites and propane instead of the stoichiometric decomposition of any potential carbonaceous residues formed during propylene treatment into propylene. We speculate that propylene reacts with $H_2O/CO_2$ to liberate Zr—O site pairs. As an example, propylene may react with and remove strongly-bound $H_2O$ to form propanols, the hydration product of propylene:

$$C_3H_6 + HO—(Zr—O)—H \leftrightarrows C_3H_7OH + (Zr—O) \quad (2)$$

The rate rapidly decreased to 2.8 µmol m$^{-2}$h$^{-1}$ within 3 ks, a comparable value to that derived from the original ZrO$_2$ (I723-O7.2) without propylene treatment. A treatment in O$_2$ for 3.6 ks (denoted as T723-O3.6(1)) restored the steady-state rates to 2.6 µmol m$^{-2}$h$^{-1}$, as shown in FIG. 2.

Effect of Dimethyl Ether (DME) Treatment on Propane Dehydrogenation Rate at 723 K After an oxidative treatment, the catalysts were exposed to DME (10 kPa at 723 K for 1.8 ks; T723-DME1.8(1)). This treatment led to an areal PDH rate of 110 µmol m$^{-2}$h$^{-1}$, a value that is about 40 times higher than those observed after O$_2$ treatments (i.e., I723-O7.2 and T723-O3.6(1), 2.6 µmol m$^{-2}$h$^{-1}$). The DME treatment also enhances the formation rate of C$_1$ (i.e., methane, rate denoted as r$_{C1}$) and C$_2$ (i.e., ethylene and ethane, rate denote as r$_{C2}$). As shown in FIG. 3$a$, the areal methane formation rate increased by about 280 times to 18 µmol m$^{-2}$h$^{-1}$ as compared to the sample without the DME treatment (0.06 µmol m$^{-2}$h$^{-1}$). The C$_1$/C$_2$ molar ratio is near unity (FIG. 3$b$) suggesting that methane forms from propane via hydrogenolysis and cracking, as shown in Equations 3a and 3b, respectively, instead of via the stoichiometric consumption of any DME-derived organic residues.

$$C_3H_8 \leftrightharpoons C_2H_4 + CH_4 \tag{3a}$$

$$C_3H_8 + H_2 \leftrightharpoons C_2H_6 + CH_4 \tag{3b}$$

The removal of the H$_2$ co-feed (between 14.5 ks and 15.1 ks) led to an additional two-fold increase of PDH rate (to 246 µmol m$^{-2}$h$^{-1}$, reflecting the kinetic inhibition of rates by H$_2$ previously shown for PDH reaction on ZrO$_2$ at 823-873 K [5]. FIG. 3$c$ shows dehydrogenation rates (normalized by mass) on ZrO$_2$ catalyst after DME treatment and also on previously reported Cr [9], Pt [10-12], Ru [9], and ZrO$_2$ [1] based catalysts. The initial PDH rates (10 mol kg$^{-1}$h$^{-1}$) after T723-DME1.8(1) treatment (13.7 kPa C$_3$H$_8$ without added H$_2$ at 723 K) is similar to those reported at much higher temperatures on other catalysts at 823-828 K and even higher C$_3$H$_8$ pressures (40-100 kPa, Pt: 14.5 mol kg$^{-1}$h$^{-1}$; Cr: 13 mol kg$^{-1}$h$^{-1}$; Ru: 10.7 mol kg$^{-1}$h$^{-1}$; ZrO$_2$: 7.1 mol kg$^{-1}$h$^{-1}$).

The rate increase upon removal of H$_2$ also leads to a two-fold decrease in C$_1$ formation rates (FIG. 3$a$), while the C$_1$/C$_2$ ratio increased from about unity to about 1.5 (FIG. 3$b$). The reasons for these trends remain unclear, since H$_2$ has been reported to preferentially remove reaction-derived organic residues as CH$_4$ from zeolitic solid acids that show alternate dehydrogenation routes on such residues [13].

The reintroduction of H$_2$ (12.3 kPa) restored dehydrogenation and C$_1$ (and C$_2$) formation rates to those measured before H$_2$ removal from the inlet stream (FIG. 3$a$). The C$_1$/C$_2$ molar ratios return to values near unity and increase slightly with time-on-stream (from 0.97 to 1.07) concurrently with a slight decrease in dehydrogenation and C$_1$ formation rates in a manner consistent with first-order deactivation process:

$$\frac{r_i(t_2)}{r_i(t_1)} = \exp\left(-k_{i,deac.}^{1st}(t_2 - t_1)\right) \tag{4}$$

Here, $$r_i, k_{i,deac.}^{1st},$$

and t$_m$ denote rates (i=f,d and C1 for dehydrogenation rate and C$_1$ rates, respectively), deactivation rate constant of reaction i, and time-on-stream at any time m, respectively. The values of $$k_{f,d,deac.}^{1st} \text{ and } k_{C1,deac.}^{1st}$$

values are 4.1×10$^{-2}$ks$^{-1}$ and 3.5×10$^{-1}$ks$^{-1}$, respectively. C$_1$ formation rates decrease more prominently with time-on-stream than dehydrogenation rates, leading to a concomitant increase in dehydrogenation selectivity (i.e., instantaneous selectivity ratio, r$_{f,d}$ (r$_{C_1}$)$^{-1}$, from 6 to 72 in the 11-19 ks period).

After 20 ks on stream (20-40 ks), PDH and methane formation rates continue to decrease as a function of time-on-stream, albeit more sharply for methane formation (FIG. 4$a$). The PDH rate eventually asymptotically approaches a value that is comparable to those measured without DME/propylene treatments. Excess amount of methane formation occurs, when considering stoichiometric cracking and hydrogenolysis reactions (in Eqs. 3a and 3b, respectively), leading to the C$_1$/C$_2$ molar ratios larger than unity at 20-40 ks times on stream. The excess methane suggests the removal of carbonaceous deposits in the form of methane catalyzed by Zr—O site pairs, previously seen during propane dehydrogenation on zeolites at comparable conditions [13]. These carbonaceous deposits are likely derived from the coupling of alkenes and deeper dehydrogenation products, which represent the amount of alkene products that do not escape the catalyst's surface but accumulates in a semi-batch form. After 40 ks on stream, the rate of deactivation decreases and C$_1$/C$_2$ molar ratios become smaller than unity (FIG. 4$b$) with reasons not clearly understood.

We define time period of time-on-stream as: 0) 11-19 ks, 1) 20-25 ks, 2) 25-30 ks, 3) 30-35 ks, 4) 35-40 ks, 5) 40-45, and 6) 45-51 ks. FIG. 4$c$ plots the averaged k$_{f,d,deac.}^{1st}$ and C$_1$-to-C$_2$ molar ratios within each time period as a function of the corresponding time period. It can be seen from FIG. 4$c$ that the deactivation rate constant almost commensurately (except for time period 4)) increases and decreases with the value of the C$_1$-to-C$_2$ molar ratio. These observations lead us to speculate that the carbonaceous deposits titrate Zr—O site pairs and are the cause of on-stream deactivation. As the amount of carbonaceous deposits increase initially, the observed deactivation rate constants and C$_1$-to-C$_2$ molar ratios in time periods 0)-to-3) also increase. Then, as the carbonaceous deposit titrates Zr—O site pairs that catalyze the PDH, propane cracking/hydrogenation, and the hydrogenolysis of the carbonaceous deposit, the PDH rate, k$_{f,d,deac.}^{1st}$ and C$_1$-to-C$_2$ molar ratios decreases, approaching to a steady-state value in the time period of 4)-to-6). The PDH rate eventually drops down to the activity measured after initial oxidative treatment, suggesting that the carbonaceous deposit does not titrate all the ZrO$_2$ sites.

In summary, these results suggest that alkene/DME treatments likely lead to rate enhancements via the reactions between alkene/DME and H$_2$O/CO$_2$. The decrease in rate after DME treatments may reflect the gradual accumulation of carbonaceous deposit.

Sequential Dimethyl Ether (DME) Treatment Effects on Propane Dehydrogenation Rate at 723 K The reproducibility of DME treatments were examined by subsequent treatments (DME, 10 kPa for 1.8 ks, T723-DME1.8(2)), after 4% $O_2$/He for 3.6 ks (T723-O3.6(2)). FIGS. 5b and FIG. 5c show the PDH areal rate and $C_1$ formation rate measured after T723-DME1.8(2) and T723-DME0.3(1), respectively; those measured after the first of such treatment is shown in FIG. 5a (shown also in FIG. 4a). The T723-O3.6(2) and T723-DME1.8(2) protocols led to similar initial rates (130 $\mu$mol m$^{-2}$h$^{-1}$ and 27 $\mu$mol m$^{-2}$h$^{-1}$ vs. 110 $\mu$mol m$^{-2}$h$^{-1}$ and 18 $\mu$mol m$^{-2}$h$^{-1}$ for dehydrogenation and $C_1$ rates after the first and second treatments, respectively). The removal of propane from the inlet stream (57.2-59.6 ks) immediately suppressed all propylene formation but not all the $C_1$ formation, consistent with the presence and gradual removal of reaction-derived organic residues as $C_1$. Restoring the propane flow (from 0 kPa to 13.7 kPa) recovered the propane dehydrogenation rate (continuing previous rate trend, increased from 0 to 75 $\mu$mol m$^{-2}$h$^{-1}$) and the methane formation rate (continuing previous rate trend, increased from 0 to 1.2 $\mu$mol m$^{-2}$h$^{-1}$).

Repeating the $O_2$ treatment for 3.6 ks (T723-O3.6(3)) and following this with a DME treatment (10 kPa) for a shorter duration of 0.3 ks (T723-DME0.3(1)) leads to initial PDH and methane areal rates of 189 $\mu$mol m$^{-2}$h$^{-1}$ and 38 $\mu$mol m$^{-2}$h$^{-1}$, respectively, as shown in FIG. 5c, which are even higher than those obtained after previous DME treatments of longer duration (i.e., T723-DME1.8(1) and T723-DME1.8(2)). Such trends and observations may reflect a hydrodynamic delay upon introduction of reactants, leading to initial rate measurements that do not reflect the intended steady-state propane and $H_2$ pressures. The deactivation of the catalyst, as reflected by the decrease in PDH areal rate, is less significant after DME treatment for 0.3 ks compared with those after DME treatment for 1.8 ks. FIG. 6 plots the $C_1$-to-$C_2$ ratio as a function of time-on-stream for those measured after T723-DME1.8(1) and T723-DME0.3(1). Although $C_1/C_2$ molar ratios start at unity in both cases, they much more gradually and to a lesser extent after the T723-DME0.3(1) than after the T723-DME1.8(1) treatment, suggesting that the carbonaceous deposit accumulation in T723-DME0.3(1) treatment is less significant, thereby leading to the catalyst's longer life time. The DME partial pressure and treatment duration effects on the PDH rate and catalyst lifetime will be part of our future study.

After T723-DME0.3(1) and PDH rate measurements, the $ZrO_2$ catalyst was regenerated again via oxidative treatment (T723-O3.6(4)). The propane dehydrogenation rate shows slightly lower areal rates of 2.2 $\mu$mol m$^{-2}$h$^{-1}$ compared with those stable rates measured after the initial oxidative treatment (I723-O7.2, 2.6 $\mu$mol m$^{-2}$h$^{-1}$).

The $CO_2$ evolved during the oxidative treatments (i.e., T723-O3.6(2), T723-O3.6(3), and T723-O3.6(4)) provides quantitative information regarding the cumulative amount of reaction-derived organic residues formed and left on the catalyst from (i) DME treatment and (ii) propane dehydrogenation reactions. Table 2 shows the amounts of $CO_2$ evolved during each $O_2$ treatment. DME treatments (0.3-1.8 ks) together with propane dehydrogenation reaction deposit $2.5\times10^{-4}$ mol (18 C nm$^{-2}$) to $2.8\times10^{-4}$ mol (21 C nm$^{-2}$) of carbon on the $ZrO_2$ catalyst, whereas a direct DME treatment for 0.3 ks (i.e., T723-DME0.3(2)), without performing propane dehydrogenation reaction, leads to the formation of $1.2\times10^{-4}$ mol of carbon (9 C nm$^{-2}$).

TABLE 2

| | Summary of $CO_2$ generated during treatment in 4 kPa $O_2$ (balanced in He) after various DME treatments before or after propane dehydrogenation reactions | | |
| --- | --- | --- | --- |
| Entry | Treatment | Carbon source | $CO_2$ per surface area (molecule nm$^{-2}$) |
| 1 | T723-O3.6(2) | T723-DME1.8(1); PDH reaction | 18 |
| 2 | T723-O3.6(3) | T723-DME1.8(2); PDH reaction | 21 |
| 3 | T723-O3.6(4) | T723-DME0.3(1); PDH reaction | 20 |
| 4 | T723-O3.6(5) | T723-DME0.3(2) | 9 |

Equation 5 defines the excess molar of propylene, $\chi$, formed from the catalyst after the DME treatment:

$$\chi = \int_{t_0}^{t_1} (r_{f,d,DME}(t) - r_{f,d,O})dt \cdot \varepsilon \tag{5}$$

where $r_{f,d,DME}(t)$, $r_{f,d,O}$, and $\varepsilon$ are the forward dehydrogenation rate after DME treatment at any time on stream t, the steady-state forward dehydrogenation rate after $O_2$ pretreatment (i.e., I723-O7.2), and the catalyst surface area, respectively. For T723-DME1.8(1), $\chi$ is $3.5\times10^{-3}$ mol (i.e., 263 nm$^{-2}$), which is more than one order of magnitude higher than the carbon deposited by DME treatment (Entry 4, Table 2). If the reaction between carbonaceous deposit and propane occurs via a stoichiometric reaction, the H-atom derived from propane dehydrogenation is sufficient to hydrogenate all the deposited carbon from DME treatment (i.e., 9 nm$^{-2}$) into $CH_4$ with $6.0\times10^{-3}$ mol of excess. Therefore, we conclude that propane dehydrogenation occurs catalytically on the $ZrO_2$ surfaces.

Effect of Dimethyl Ether (DME) Treatment on Water Removal Revealed by Temperature Programmed Desorption (TPD)

The as prepared $ZrO_2$ was treated at 323 K in He for 7.2 ks before TPD. The temperature was increased at 0.03 K s$^{-1}$ from 323 K to 723 K in 1 kPa DME (balanced with He, 0.83 cm$^3$s$^{-1}$). The $H_2O$ and methanol evolution profile, plotted against the temperature, is shown in FIG. 7. As temperature increases, water desorption occurs at 373 K and 523 K, whereas methanol formation begins to occur at 520 K. The formation of water suggests the stoichiometric reaction of DME and surface hydroxyls occurs via:

$$CH_3OCH_3 + HO-(Zr-O)-H \rightleftharpoons 2CH_3OH + (Zr-O) \tag{6}$$

The methanol evolvement clearly demonstrates the successful removal of water by the DME hydration reaction. This removal of water exposes stoichiometric Zr—O site pairs, as suggested in Equation 6. In contrast to what has been shown in FIG. 1, both methanol and water signals decrease to below detection limits at 723 K, reflecting the complete removal of water (and surface hydroxyls) via DME hydration at 723 K.

Figure 1:
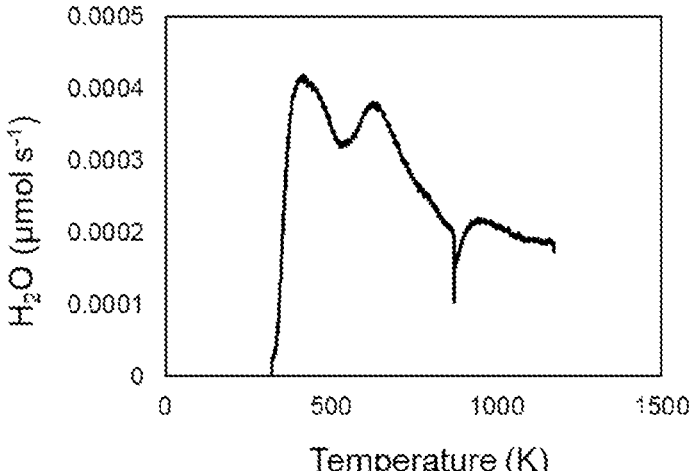
FIG. 1. $H_2O$ desorption molar rate plotted as a function of temperature during temperature programmed oxidation (TPO) of as prepared $ZrO_2$ catalysts (0.2 g, He and 25 kPa $H_2$ treated at 873 K) from 323 K to 873 K (0.167 K $s^{-1}$) and from 873 K to 1173 K.

Origin of Rate Enhancement from DME Treatment and Apparent Barrier Measurements of PDH Rate on DME-Cleaned $ZrO_2$ Surfaces Thermal treatment (i.e., treatments in the absence of alkene/ethers) of a new load of $ZrO_2$ catalyst at 873 K for 7.2 ks (I873-O7.2) causes the initial propane dehydrogenation to increase by about ten-fold to 26 $\mu$mol m$^{-2}$h$^{-1}$, as shown in FIG. 8, compared to the catalyst pretreated in $O_2$ at 723 K for the same duration (I723-O7.2, FIG. 1, 2.6 μmol m$^{-2}$h$^{-1}$). A subsequent DME treatment at 723 K for 0.3 ks (T723-DME0.3(1)) increases the rate to 94 μmol m$^{-2}$h$^{-1}$, which is slightly smaller than that measured in previous load after T723-DME1.8(1) (110 μmol m$^{-2}$h$^{-1}$, FIG. 2a) for the sample pretreated at 723 K (I723-O7.2). We speculate that the high temperature thermal treatment is able to generate more active Zr—O site pairs via water/CO$_2$ removal, as clearly indicated in FIG. 1, but such high temperature treatment simultaneously collapses the porous structure of the ZrO$_2$ and leads to decreased surface areas as previously reported for ZrO$_2$ [6]. As a result, the PDH areal rate after DME treatment at 723 K are smaller for the new load catalysts (FIG. 8, initial oxidative treatment at 873 K) than those measured for the previous load of catalysts (FIG. 2, initial oxidative treatment at 723 K).

For the new load of catalyst (i.e., I873-O7.2), a follow-up O$_2$ treatment at 723 K (T723-O3.6(1)) causes the PDH rate (13.7 kPa propane, 12.3 kPa H$_2$, 723 K) to decrease to 2.5 μmol m$^{-2}$h$^{-1}$, which is comparable to the rate measured after an initial O$_2$ pretreatment at 723 K of the previous load (i.e., 2.6 μmol m$^{-2}$h$^{-1}$, I723-O7.2, FIG. 1). As the oxidative treatments remove carbon deposits derived from previous DME treatment and/or PDH rate measurements as H$_2$O and CO$_2$, results in FIG. 8b suggest that (i) the H$_2$O and/or CO$_2$ generated during oxidative treatment (T723-O3.6) titrates the Zr—O sites and (ii) an oxidative treatment at 873 K liberates more vacant Zr—O site pair than that at 723 K. A subsequent DME treatment for 0.3 ks (T723-DME0.3(2)), however, restores the propane dehydrogenation activity to the identical level as previous DME treatment (T723-DME0.3(1)), in no regards of the PDH activity from previous measurement after oxidative treatment. This observation further confirms that DME can regenerate Zr—O site pairs in a reproducible manner.

Attempting to recover the Zr—O site pairs via oxidative treatments at 873 K with a He purge at 873 K for 3.6 ks (T873-O3.6(1)) or overnight (T873-O3.6(2))) lead to areal PDH rates of 10 μmol m$^{-2}$h$^{-1}$ and 17 μmol m$^{-2}$h$^{-1}$, respectively. These oxidative treatments at 873 K did not fully recover of the PDH rate after initial oxidative treatment (i.e., 26 μmol m$^{-2}$h$^{-1}$, after I873-O7.2). We speculate that the extent of regeneration of Zr—O site pairs via oxidative and a following He treatments at 873 K depends on (i) the amount of carbonaceous residue formed from previous treatment(s) and PDH rate measurements, which dictates the amount of CO$_2$ and H$_2$O formed during the oxidative treatment, and (ii) the duration at which the catalyst resides in He. The inconsistent rate measured after oxidative treatments reflects the inconsistent amount of Zr—O site regenerated after these treatments. The DME treatments at 723 K (T723-DME0.3(i), i=1-4), however, always lead to reproducible reactivities of about 90 μmol m$^{-2}$h$^{-1}$, irrespective of the PDH rate measured after preceding oxidative treatments. These observations further confirm that DME can remove irreversible titrants of H$_2$O and CO$_2$ generated during oxidative treatments and exposes ZrO$_2$ surface to an identical extent.

We further corroborate the effect of DME treatments by measuring the apparent PDH barrier on a DME treated ZrO$_2$ catalyst. The PDH rate was measured at 13.7 kPa propane pressure and 12.3 kPa H$_2$ pressure from 723 K to 873 K. The PDH rate constant, obtained by normalizing the measured PDH rate by the arithmetic average of the inlet and outlet propane pressure, is plotted in an Arrhenius plot (FIG. 9). This measured value is more than 40 kJ mol$^{-1}$ smaller than what has been reported on ZrO$_2$ catalysts [1] but appears comparable to the value derived from density functional theory (DFT-D3) calculation derived barrier (106 kJ mol$^{-1}$) of PDH on a stoichiometric monoclinic ZrO$_2$ (−111) surface. We suspect that previous measurements in the absence of DME treatments are unable to expose Zr—O site pairs at lower temperatures (e.g., <823 K). Thus, these previous reports underestimate the PDH turnover rates to a greater extent at lower temperatures and hence overestimate the apparent PDH barrier. The consistency between experimentally and theoretically derived barrier corroborates that DME (and alkene) hydration reaction removes water bound to Zr—O site pairs and exposes these site pairs as the active sites for PDH reaction.

Figures 3A, 3B, 3C:
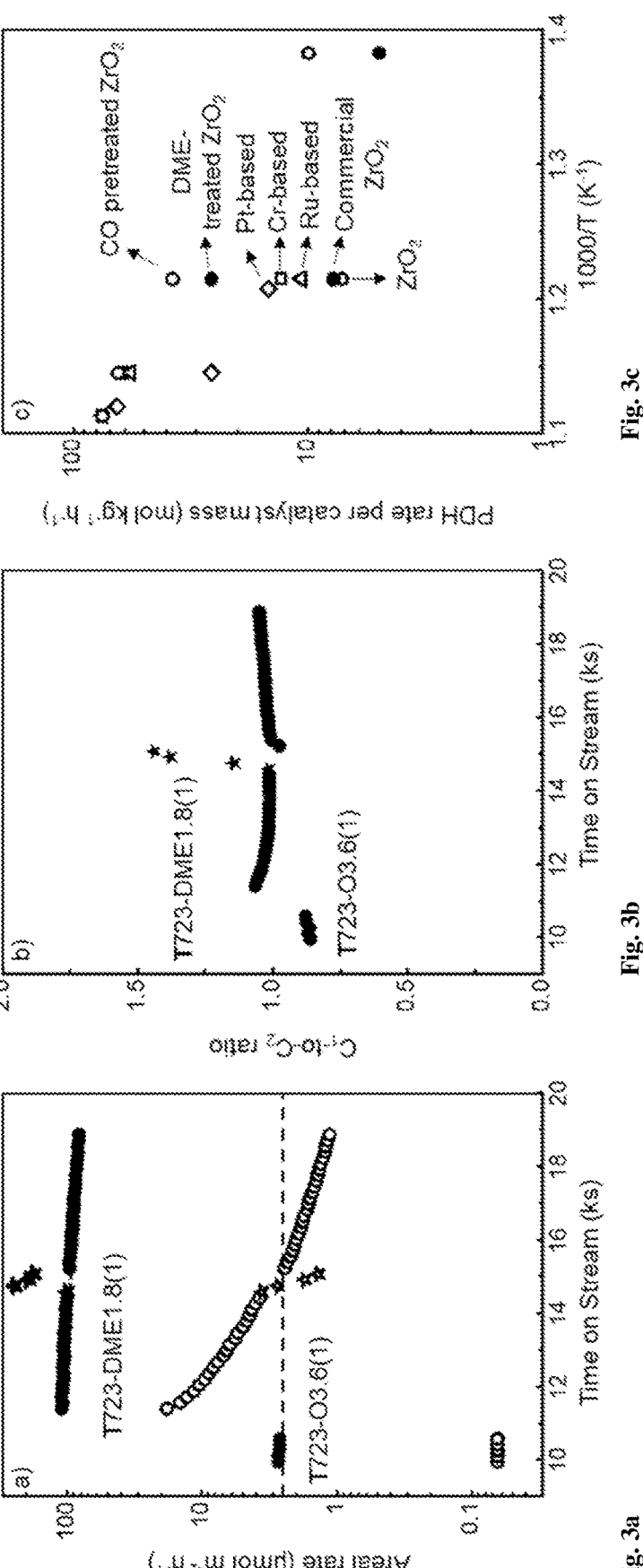
FIGS. 3a-c. a) Areal rates of PDH ($r_{f,d}$, solid symbols) and $C_1$ formation ($r_{C1}$), and b) $C_1$-to-$C_2$ ratio during propane dehydrogenation reaction on $ZrO_2$ catalyst (13.7 kPa $C_3H_8$, 12.3 kPa $H_2$, 723 K, I723-O7.2); color indicates the treatment seen prior to the reaction (magenta: $O_2$; brown: DME)

Effect of Dimethyl Ether (DME) Treatment on Propane Dehydrogenation Rate at 823 K and the Operation in Cyclic Mode Treatment of DME (10 kPa) at 823 K for a duration of 0.06 ks (T823-DME0.06) leads to an initial PDH rate measured at 13.7 kPa propane, 12.3 kPa H$_2$, and 823 K of 643 μmol m$^{-2}$h$^{-1}$, as shown in FIG. 10a. The catalyst then rapidly deactivates with the first-order deactivation rate constant of 2.2×10$^{-1}$ ks$^{-1}$. Increasing the H$_2$ partial pressure from 12.3 kPa to 50 kPa leads to an instantaneous decrease in the rate from 218 μmol m$^{-2}$h$^{-1}$ to 144 μmol m$^{-2}$h$^{-1}$ (FIG. 10a), which is consistent with the H$_2$ inhibition observed at 723 K (FIG. 3a). Areal propane dehydrogenation rates increase to 168 μmol m$^{-2}$h$^{-1}$ following an oxidative treatment at 823 K for 3.6 ks (T823-O3.6(1)). The PDH rate then increases gradually to a maximum at 375 μmol m$^{-2}$h$^{-1}$ before decaying to 318 μmol m$^{-2}$h$^{-1}$ with time-on-stream. Oxidative treatment at 723 K for 3.6 ks (T723-O3.6(5)) causes the PDH rate at about 220 μmol m$^{-2}$h$^{-1}$ at 823 K, as shown in FIG. 10b. The PDH rate is comparable with that obtained initially after T823-O3.6(1) (168 μmol m$^{-2}$h$^{-1}$, FIG. 10a), but it does not undergo similar transient after T823-O3.6(1). These inconsistent areal PDH rate, obtained after oxidative treatments, suggests that the number of exposed Zr—O site pairs may vary according to previous treatment conditions or the duration of PDH rate measurements.

The following three direct DME treatments in FIG. 10b with lower DME pressure (1 kPa, denoted as T823DME1kPa(x), where x=1, 2, or 3) enhances the PDH rate to about 420 μmol m$^{-2}$h$^{-1}$ each time. After each DME treatment, the PDH rate rapidly decreases to about 300 μmol m$^{-2}$h$^{-1}$ within 1.5 ks, as shown in FIG. 10b; the first-order deactivation rate constant is about 2.2-2.5×10$^{-1}$ ks$^{-1}$. These observations lead us to conclude that (i) part of the reason for the on-stream deactivation is mediated by the water poisoning from ppm levels of water in the reactant stream, and (ii) the DME treatments are highly reproducible and can regenerate Zr—O site pairs even without oxidative treatments. The PDH rate does not, however, recover to that measured after the first DME treatment at 823 K (i.e., 643 μmol m$^{-2}$h$^{-1}$, T823-DME0.06.

Subsequent oxidative treatments (T823-O3.6(2)) leads to an areal PDH rate of 267 μmol m$^{-2}$h$^{-1}$. The followed up DME treatments at 573 K for 0.6 ks (T573-DME1kPa0.6) or 0.06 ks (T573-DME1kPa0.06) lead to the areal PDH rates of 611 μmol m$^{-2}$h$^{-1}$ and 837 μmol m$^{-2}$h$^{-1}$, respectively, which are comparable (or even higher) to that obtained after T823-DME0.06. These results suggest that DME treatments at 573 K, 1 kPa of DME with durations of 0.06 ks are effective and lead to the removal of H$_2$O and CO$_2$. The final, oxidative treatment at 823 K for 3.6 ks (T823-O3.6(3)) leads to a PDH rate of about 175 μmol m$^{-2}$h$^{-1}$. Once again, the oxidative treatments (e.g., T823-O3.6(1), T823-O3.6(2), and T823-O3.6(3)) do not reset the $ZrO_2$ catalyst to a consistent starting point but instead exhibit a memory effect.

In conclusion, the DME treatment promotes PDH rate but less significantly at 823 K; the repetitive DME treatments reset the PDH rate in a consistent manner; the DME treatment is able to remove water and regenerate active sites at temperature as low as 573 K with lower DME exposure (i.e., 1 kPa).

REFERENCES

[1] Y. Zhang, Y. Zhao, T. Otroshchenko, H. Lund, M.-M. Pohl, U. Rodemerck, D. Linke, H. Jiao, G. Jiang, E. V. Kondratenko, Control of coordinatively unsaturated Zr sites in ZrO 2 for efficient C—H bond activation, Nature communications, 9 (2018) 1-10.

[2] M.-Y. He, J. G. Ekerdt, Temperature-programmed studies of the adsorption of synthesis gas on zirconium dioxide, Journal of Catalysis, 87 (1984) 238-254.

[3] J. Kondo, H. Abe, Y. Sakata, K.-i. Maruya, K. Domen, T. Onishi, Infrared studies of adsorbed species of H2, CO and CO 2 over ZrO 2, Journal of the Chemical Society, Faraday Transactions 1: Physical Chemistry in Condensed Phases, 84 (1988) 511-519.

[4] J. Kondo, Y. Sakata, K. Domen, K.-i. Maruya, T. Onishi, Infrared study of hydrogen adsorbed on ZrO2, Journal of the Chemical Society, Faraday Transactions, 86 (1990) 397-401.

[5] T. F. J. C. D. E. Iglesia, Stabilization of zirconium oxide catalysts for paraffin dehydrogenation by co-feed hydrogen Unpublished results.

[6] S. Xie, E. Iglesia, A. T. Bell, Water-assisted tetragonal-to-monoclinic phase transformation of ZrO2 at low temperatures, Chemistry of materials, 12 (2000) 2442-2447.

[7] M.-Y. He, J. G. Ekerdt, Methanol formation on zirconium dioxide, Journal of Catalysis, 90 (1984) 17-23.

[8] P. Lackner, J. Hulva, E.-M. Köck, W. Mayr-Schmölzer, J. I. J. Choi, S. Penner, U. Diebold, F. Mittendorfer, J. Redinger, B. Klötzer, Water adsorption at zirconia: from the ZrO 2 (111)/Pt 3 Zr (0001) model system to powder samples, Journal of Materials Chemistry A, 6 (2018) 17587-17601.

[9] T. Otroshchenko, S. Sokolov, M. Stoyanova, V. A. Kondratenko, U. Rodemerck, D. Linke, E. V. Kondratenko, ZrO2-Based Alternatives to Conventional Propane Dehydrogenation Catalysts: Active Sites, Design, and Performance, Angewandte Chemie International Edition, 54 (2015) 15880-15883.

[10] P. L. De Cola, R. Gläser, J. Weitkamp, Non-oxidative propane dehydrogenation over Pt—Zn-containing zeolites, Applied Catalysis A: General, 306 (2006) 85-97.

[11] J. J. Sattler, I. D. Gonzalez-Jimenez, L. Luo, B. A. Stears, A. Malek, D. G. Barton, B. A. Kilos, M. P. Kaminsky, T. W. Verhoeven, E. J. Koers, Platinum-promoted Ga/Al2O3 as highly active, selective, and stable catalyst for the dehydrogenation of propane, Angewandte Chemie, 126 (2014) 9405-9410.

[12] H. N. Pham, J. J. Sattler, B. M. Weckhuysen, A. K. Datye, Role of Sn in the regeneration of Pt/γ-Al2O3 light alkane dehydrogenation catalysts, ACS catalysis, 6 (2016) 2257-2264.

[13] P. M. Kester, E. Iglesia, R. Gounder, Parallel Alkane Dehydrogenation Routes on Brøsted Acid and Reaction-Derived Carbonaceous Active Sites in Zeolites, The Journal of Physical Chemistry C, 124 (2020) 15839-15855.

The invention claimed is:

1. A method of catalytic dehydrogenation of a light alkane gas, the method comprising steps:
   (a) pretreating a metal oxide catalyst comprising surface-bound $H_2O$ or $CO_2$ with dimethylether (DME) to obtain dehydroxylation or decarboxylation of the catalyst via DME reactions with the $H_2O$ or $CO_2$, respectively, providing a DME-cleaned catalyst, the pretreating step occurring prior to contacting the catalyst with the alkane gas; and thereafter,
   (b) reacting the alkane gas catalytically on the DME-cleaned catalyst in a dehydrogenation reaction, under conditions wherein the pretreating improves product yield of the reaction, wherein:
   the pretreating improves product yield at least 2-fold compared with a comparable reaction without the pretreating step,
   the metal oxide is $ZrO_2$, and
   the pretreating is performed within a temperature range of 323-900 K.

2. The method of claim 1 wherein the pretreating is performed at a temperature within a range of 323-873 K.

3. The method of claim 1 wherein the pretreating is performed at a temperature of 723 K.

4. The method of claim 1, wherein the alkane is propane.

5. The method of claim 1, wherein the reaction product is an alkene.

6. The method of claim 1, wherein:
   the alkane is propane; and
   the reaction product is an alkene.

7. The method of claim 1, wherein the pretreating step further comprises a pretreatment with oxygen prior to or following the pretreatment with DME.

8. The method of claim 1, wherein the pretreating is performed at a temperature of 573 K, at a pressure of 1 kPa of DME, and with a duration of 0.06 ks.

9. The method of claim 1, performed in cyclic mode, wherein the method further comprises subsequent steps:
   (c) re-treating the catalyst with DME;
   (d) reacting additional alkane gas catalytically on the DME-re-treated catalyst in a dehydrogenation reaction; and
   (e) repeating steps (c) and (d) in a cyclic mode.

10. The method of claim 9, wherein in each DME re-treatment resets the dehydrogenation rate consistently.

11. The method of claim 9, wherein the pretreating step and each re-treating step is performed at a temperature within a range of 323-873 K.

12. The method of claim 9, wherein the pretreating step and each re-treating step is performed at a temperature of 723 K.

13. The method of claim 9, wherein the alkane is propane.

14. The method of claim 9, wherein the reaction product is an alkene.

15. The method of claim 9, wherein:
   the alkane is propane; and
   the reaction product is an alkene.

16. The method of claim 9, wherein the pretreating step further comprises a pretreatment with oxygen prior to or following the pretreatment with DME.

17. The method of claim 9, wherein the pretreating step and each re-treating step is performed at a temperature of 573 K, at a pressure of 1 kPa of DME, and with a duration of 0.06 ks.

* * * * *